United States Patent
Trotta

(10) Patent No.: US 6,663,648 B1
(45) Date of Patent: *Dec. 16, 2003

(54) BALLOON CATHETER WITH FLOATING STIFFENER, AND PROCEDURE

(75) Inventor: Thomas N. Trotta, Sunny Isles Beach, FL (US)

(73) Assignee: Cordis Corporation, Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 211 days.

(21) Appl. No.: 09/594,859

(22) Filed: Jun. 15, 2000

(51) Int. Cl.[7] .................. A61M 29/00; A61M 37/00
(52) U.S. Cl. .............. 606/194; 604/103.09; 604/96.01; 604/103
(58) Field of Search .............................. 604/196, 96.01, 604/103.04, 103, 915; 606/194, 919, 921; 600/435, 466, 467

(56) References Cited

U.S. PATENT DOCUMENTS

| | | | |
|---|---|---|---|
| 4,762,129 A | 8/1988 | Bonzel | |
| 4,838,268 A | 6/1989 | Keith et al. | |
| 4,917,666 A | 4/1990 | Solar et al. | |
| 4,943,278 A | 7/1990 | Euteneuer et al. | |
| 5,040,548 A | 8/1991 | Yock | |
| 5,061,273 A | 10/1991 | Yock | |
| 5,156,594 A | 10/1992 | Keith | |
| 5,217,482 A | 6/1993 | Keith | |
| 5,300,025 A | 4/1994 | Wantink | |
| 5,346,505 A | 9/1994 | Leopold | |
| 5,370,616 A | 12/1994 | Keith et al. | |
| 5,395,334 A | 3/1995 | Keith et al. | |
| 5,425,711 A | 6/1995 | Ressemann et al. | |
| 5,458,605 A | 10/1995 | Klemm | |
| 5,490,837 A | 2/1996 | Blaeser et al. | |
| 5,522,818 A | 6/1996 | Keith et al. | |
| 5,531,690 A | 7/1996 | Solar | |
| 5,538,510 A | * 7/1996 | Fontirroche et al. | ........ 604/265 |
| 5,567,203 A | 10/1996 | Euteneuer et al. | |
| 5,658,251 A | 8/1997 | Ressemann et al. | |
| 5,702,439 A | 12/1997 | Keith et al. | |

(List continued on next page.)

FOREIGN PATENT DOCUMENTS

| | | |
|---|---|---|
| EP | 0 428 976 A1 | 5/1991 |
| EP | 0 580 845 B1 | 2/1994 |
| EP | 0 608 853 A2 | 8/1994 |
| EP | 0 715 863 A2 | 6/1996 |
| EP | 0 925 801 A1 | 6/1999 |
| WO | 92/00775 | 1/1992 |
| WO | 92/17236 | 10/1992 |
| WO | 95/24236 | 9/1995 |
| WO | WO 00/24451 | 5/2000 |

Primary Examiner—Michael J. Milano
Assistant Examiner—Gwen Phanijphand
(74) Attorney, Agent, or Firm—Michael W. Montgomery

(57) ABSTRACT

A balloon dilatation catheter has a relatively stiff and strong proximal cannula made of a material such as for example metal hypotubing. The distal end of the catheter includes an inflatable medical device or balloon, an inflation lumen and a guidewire lumen. A transition assembly is positioned between the proximal cannula and the distal end section. This transition assembly has a stiffening member within a transition tube, and provides for a flexible transition between the two components of diverse stiffness, namely the proximal cannula and the flexible distal end portion. A proximal end of the stiffening member may float within a distal end of the proximal cannula, but the stiffening member distal end is affixed to the shaft. The dilatation catheter may have a rapid exchange configuration, and is generally used in conjunction with a guiding catheter. During a procedure when the catheters are within the vascular system, the transition section of the dilatation catheter readily follows curved portions of the inserted guiding catheter.

18 Claims, 3 Drawing Sheets

U.S. PATENT DOCUMENTS

| | | |
|---|---|---|
| 5,728,067 A | 3/1998 | Enger |
| 5,782,809 A | 7/1998 | Umeno et al. |
| 5,797,874 A | 8/1998 | Spears |
| 5,807,355 A | 9/1998 | Ramzipoor et al. |
| 5,823,995 A | 10/1998 | Fitzmaurice et al. |
| 5,899,891 A * | 5/1999 | Racz ........................ 604/264 |
| 5,931,812 A | 8/1999 | Andersen et al. |
| 5,980,486 A | 11/1999 | Enger |
| 6,004,291 A | 12/1999 | Ressemann et al. |
| 6,010,521 A * | 1/2000 | Lee et al. ................. 606/194 |
| 6,030,405 A | 2/2000 | Zarbatany et al. |
| 6,036,670 A | 3/2000 | Wijeratne et al. |
| 6,066,114 A * | 5/2000 | Goodin et al. .............. 606/194 |
| 6,129,707 A * | 10/2000 | Cryer ...................... 604/96.01 |
| 6,129,708 A | 10/2000 | Enger |
| 6,139,525 A * | 10/2000 | Davis-Lemessy et al. .. 604/103 |
| 6,273,879 B1 | 8/2001 | Keith et al. |
| 6,322,534 B1 * | 11/2001 | Shkolnik ................. 604/96.01 |
| 6,375,458 B1 * | 4/2002 | Moorleghem et al. ......... 433/2 |

\* cited by examiner

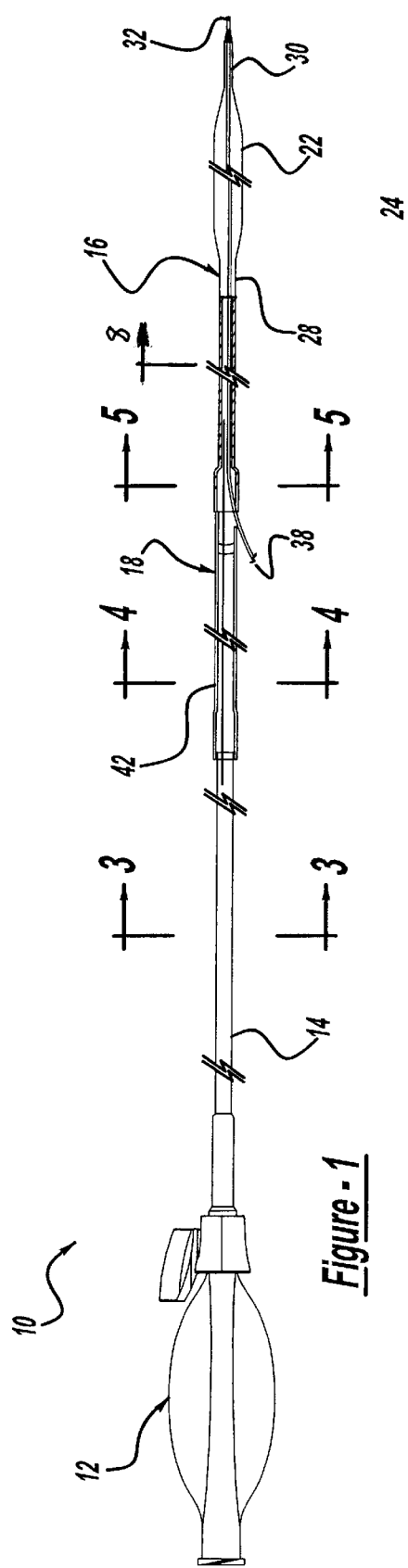
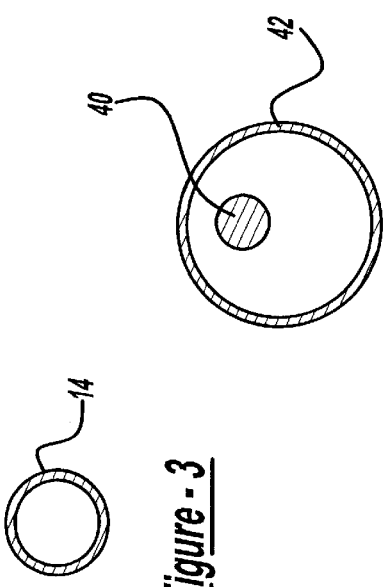
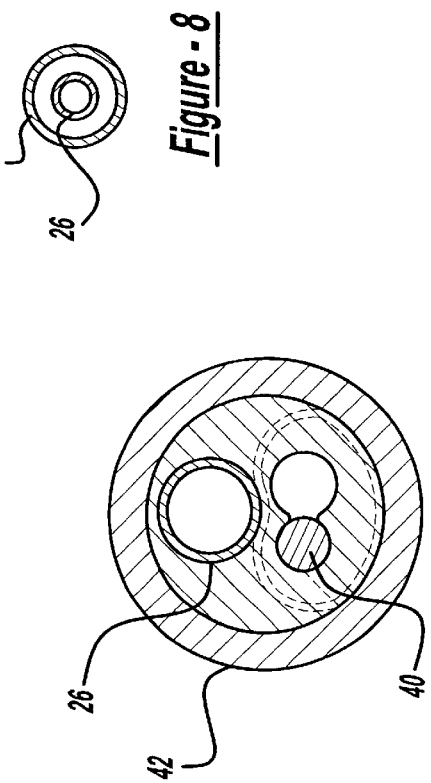

BALLOON CATHETER WITH FLOATING STIFFENER, AND PROCEDURE

BACKGROUND AND SUMMARY OF THE INVENTION

1. Technical Background

The present invention generally relates to a balloon catheter for conducting dilatation procedures within the vascular system. The balloon catheter may be used in conjunction with a guiding catheter, within which the balloon catheter is slidably moved for positioning and treatment. The balloon catheter includes an elongated, high-strength cannula or hypotube as a proximal tube component. The catheter has a distal end assembly which includes the balloon and which has a substantially greater flexibility than that of the proximal cannula. The proximal cannula and the distal end assembly are joined together by a transition assembly which has a stiffening element. The present invention improves various performance features of the catheter, including trackability, pushability, flexibility, etc.

2. Discussion

In many applications for dilatation catheters, it is desirable to provide a proximal catheter tube which is relatively stiff and of high strength so that the elongated proximal tube accepts and transmits column force, as well as torsional forces, from the proximal end of the catheter which remains outside of the body, to the distal end portion of the catheter so that the balloon is properly positioned for performing the dilatation procedure.

Proximal elongated tubes such as metal hypotubes have been proposed or used in the past for balloon catheter shafts. However, this type of stiff tubing preferably does not extend the full length of the balloon catheter. In order to maneuver through tight turns and/or constricting passageways, the distal end portion of the catheter should be quite flexible.

While having a stiff proximal hypotube and a flexible distal portion has been a desirable objective, achieving this objective is complicated by the need for providing a suitable transition between a relatively stiff elongated member and a relatively flexible elongated member. As used in this patent, the term "elongated" refers simply to having a measurable length, as opposed to implying any stretching or process that might otherwise be considered "elongation". It has been found that, when two such diverse stiffness sections interface directly with each other, there is a tendency that the catheter may kink or prolapse on itself during movement of the balloon catheter with respect to the guiding catheter. Accordingly, the balloon catheter may not move consistently and smoothly through the guiding catheter, or even reach the desired site. At times, the guiding catheter may dislodge from its desired position within the vascular system of the body.

In the past, catheters of this general type have included a transitional section between a stiff hypotube type of component and a flexible distal end portion of the catheter. A primary component of these types of transitional section approaches is the incorporation of a structure having selected flexibility or range of flexibilities generally at the transition location, whereby the stiffness at the proximal hypotube is gradually reduced toward the flexible distal portion of the catheter. In some known systems, a bridging wire is attached to the hypotube as a distally oriented extension of the hypotube, positioned within a transition section between the hypotube distal end and the distal portion of the catheter with the balloon.

With approaches such as those generally identified above, the bridge wire or a similar structure may present challenges when the balloon catheter must be passed through a tightly curved portion of the guiding catheter. There may be a tendency for the bridge wire to transfer a bending or lateral force to the walls of the guiding catheter, due to the stiffness of the bridging wire, which lateral force typically increases when the tightness of the curve increases.

It is accordingly desirable for a catheter system to have a balloon catheter which will easily navigate tight curves in the distal portion of the guiding catheter without imparting undue lateral force to the walls of the guiding catheter, which could possibly result in unintentional dislodgement of the guiding catheter due to movement of the balloon catheter. Accordingly, the present invention concentrates on the structure of a transition section between a relatively stiff proximal tube and a relatively flexible distal portion.

The present invention can also be relevant in catheters having a rapid exchange configuration, which incorporate a guidewire lumen only at a distal end portion of the catheter. Such an overall structure permits the physician to easily and rapidly exchange one balloon catheter for another, and generally avoids the need for extended or extendable length guidewires, and the issues associated with providing and handling them. Balloon catheter systems of this general type are shown in Yock U.S. Pat. No. 5,061,273 and Leopold U.S. Pat. No. 5,346,505, and their subject matter is incorporated herein by reference. Generally, by providing a guidewire exit port in a generally distal portion of the catheter, it can intensify the possibility of undesired weakness or sharp flexibility transitions of the catheter. Such weakness may be caused by abrupt flexibility differences between a distal section of the catheter having the guidewire tube and guidewire, and a proximal section of the catheter immediately proximal of the guidewire exit port. There is accordingly a preference for an improved transition structure in balloon catheters generally, and in the vicinity of the guidewire exit port of balloon catheters having a rapid exchange configuration.

In accordance with the present invention, a balloon dilatation catheter has an improved transition assembly between a relatively high-strength proximal cannula and a generally tubular distal end assembly, which is substantially more flexible than the proximal cannula. The transition assembly provides flexible bending strain relief having optimized flexibility, column strength, pull strength, and other characteristics. The transition assembly preferably includes a stiffening member within a transition tube. Moreover, the stiffening member may preferably be attached to the catheter shaft near its distal end, and float relatively freely in the catheter shaft at its proximal end.

This balloon dilatation catheter will often be used in combination with a guiding catheter, so the balloon dilatation catheter is able to smoothly follow sharp curves of the guiding catheter which may be encountered during a dilatation procedure such as angioplasty. With this combination, the transition assembly is optimized to impart a minimal lateral force on the guiding catheter, so as to avoid dislodgement of the guiding catheter from its intended position in the vascular system, as the dilatation catheter is moved within the guiding catheter.

Accordingly, a general possible object of the present invention is to provide an improved balloon dilatation catheter, combination of dilatation catheter and guiding catheter, and method for making the balloon dilatation catheter.

Another possible object of this invention is to provide an improved balloon catheter having a transition assembly which provides flexible bending strain relief during medical procedures.

Another possible object of the present invention is to provide an improved combination of balloon dilatation catheter and guiding catheter, such that during slidable positioning of the balloon dilatation catheter within the guiding catheter, the transition section readily bends in an arc, thereby minimizing the lateral force applied to the guiding catheter and avoiding dislodgement of the guiding catheter from the desired position.

Another possible object of this invention is to provide a balloon dilatation catheter which moves linearly in the distal direction inside of a guiding catheter, without undesired flexing of the transition assembly, which could hinder transmission of forces from the proximal end of the catheter outside the body to the distal end of the catheter inside the patient's body.

Another possible object of the present invention is to provide an improved balloon dilatation catheter and guiding catheter combination, which reduces the chance of having the guiding catheter become dislodged from the desired position during an angioplasty procedure.

Another possible object of this invention is to provide a balloon dilatation catheter having a transition section which reduces the incidence of kinking the catheter.

Another possible object of the present invention is to provide an improved balloon dilatation catheter and guiding catheter combination, which exhibits an advantageous ease of tracking and lower tracking force, due to having an improved transition section which forms to the shape of the guiding catheter when that transition section moves through the guiding catheter.

Another possible object of the present invention is to provide a transition section for a balloon dilatation catheter which provides a relatively larger cross-sectional area for passage of balloon inflation fluid during balloon inflation and deflation.

These and other possible objects, features and advantages of the present invention will be apparent from and clearly understood through a consideration of the following detailed description of the preferred embodiment.

BRIEF DESCRIPTION OF THE DRAWINGS

In the course of this description of preferred embodiments, reference will be made to the attached drawings, wherein:

FIG. 1 is a partially schematic generally elevational view of a preferred balloon dilatation catheter in accordance with the principles of the present invention;

FIG. 3 is a cross-sectional view along the line 3—3 of FIG. 1;

FIG. 4 is a cross-sectional view along the line 4—4 of FIG. 1;

FIG. 5 is a cross-sectional view along the line 5—5 of FIG. 1;

FIG. 8 is a cross-sectional view of the outer and inner body tubes of the catheter of FIG. 1.

DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 2:
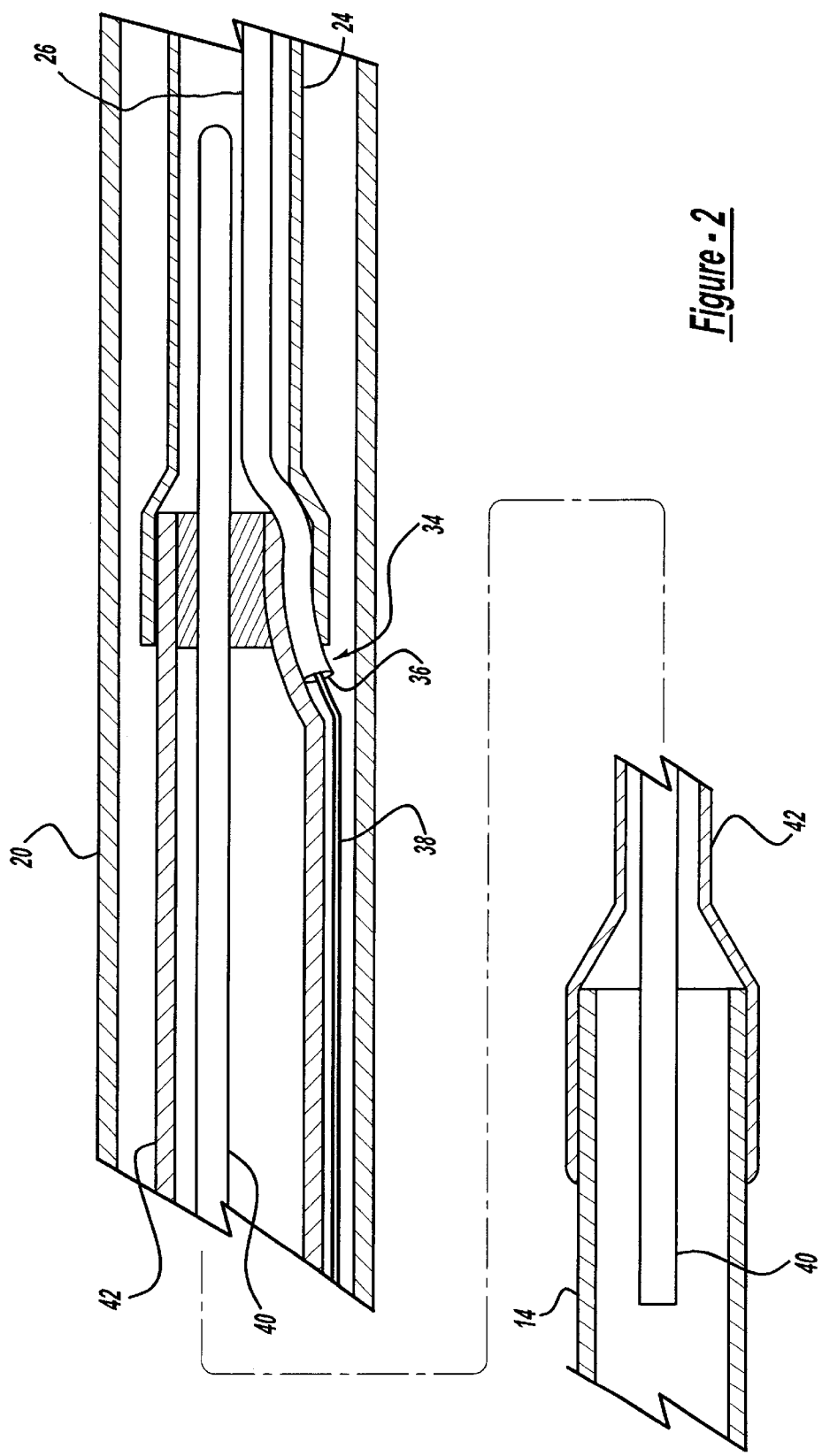
FIG. 2 is an enlarged, substantially cross-sectional view including the transition section of the catheter generally illustrated in FIG. 1, shown positioned within a guiding catheter, partially cut away and shown in transverse cross-section.
Figure 6:
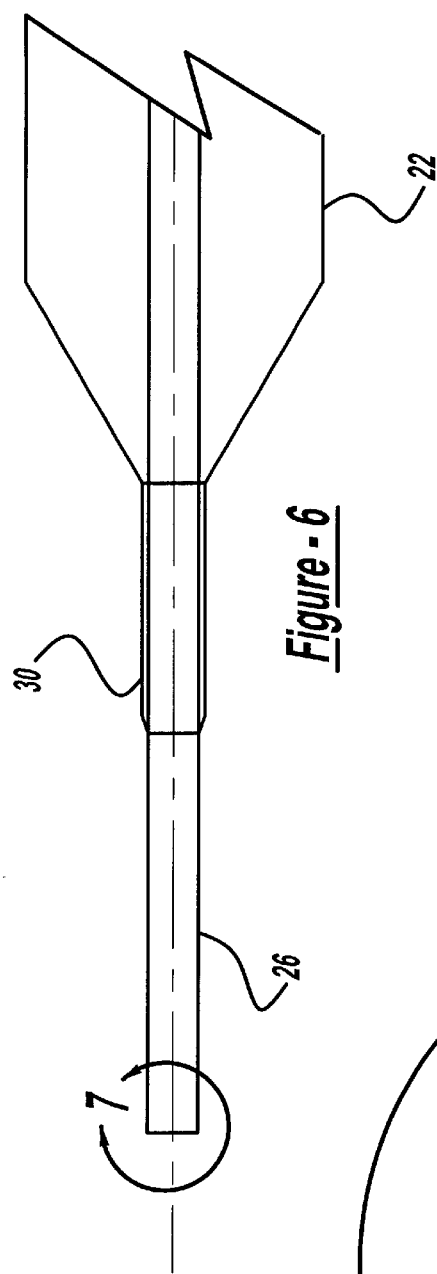
FIG. 6 is a generally diagrammatic partial view of the distal tip portion of the catheter of FIG. 1.
Figure 7:
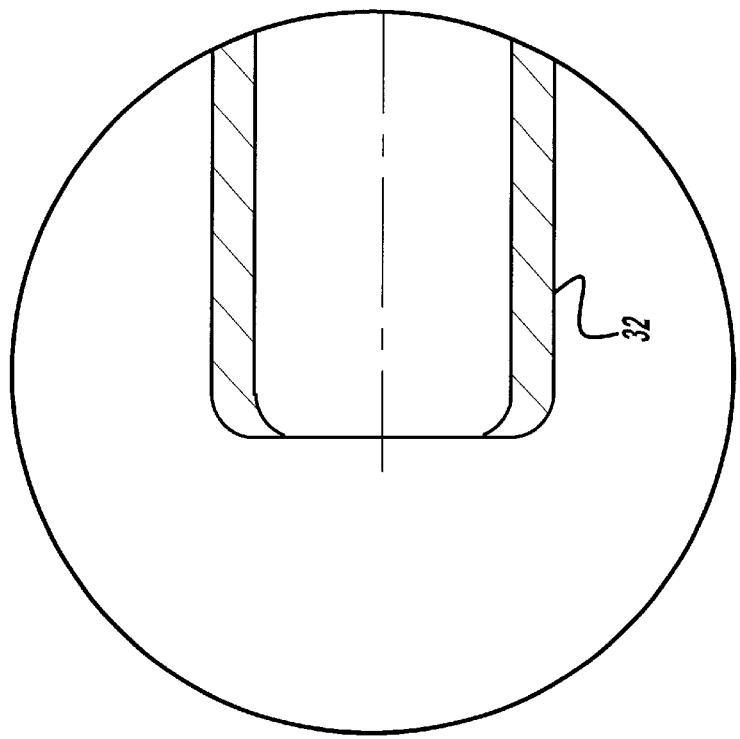
FIG. 7 is an expanded partial cross-section view of the distal end of the catheter of FIG. 6.

A preferred balloon dilatation catheter is generally designated in FIG. 1 by reference numeral 10. It includes a proximal hub assembly 12 of generally known structure for manipulating the catheter 10 from a location outside of the patient's body in a manner which is generally known in the art. An elongated, high strength proximal cannula or hypotube 14 is attached to the hub assembly 12 by a suitable structure and approach. A distal end assembly including a balloon, generally designated at 16, provides the distal portion of the catheter 10. A transition assembly, generally designated at 18, connects the flexible distal end assembly 16 to the proximal cannula 14. A guiding catheter 20 is generally depicted in FIG. 2 in sliding engagement with the balloon dilatation catheter 10.

With more particular reference to the proximal cannula 14, it is preferably made of a hypotube, typically made of metal. Some especially stiff polymers can also be used. Hypotubes include those made of stainless steel, other stiff alloys available for use within the body, nickel-titanium alloys such as nitinol, and similar materials. The proximal cannula 14 incorporates a material and structure which provides excellent load-bearing properties, including high column strength and excellent torqueability. Properties such as these permit a physician to accurately manipulate the substantial proximal length of the catheter while the catheter is inserted within and through the vascular system of the patient. Such a high-strength cannula 14 also provides responsive movement of the more distal portions of the catheter 10 in response to movements such as twisting and longitudinal movements in and out within the vascular system.

It will be appreciated that maneuvering control at this proximal portion of the balloon dilatation catheter 10 enhances the performance characteristics of, and imparts an advantageous sure-handed feel to a balloon dilatation catheter. Typically, the length of the elongated cannula plus the hub assembly is between about 100 cm and about 120 cm. A typical balloon dilatation catheter in accordance with the invention has a total length from the hub assembly to the distal tip of about 140 cm to about 160 cm.

Another particular advantage of making the proximal cannula 14 of a material such as stainless steel or other metal alloy or especially strong polymer, is that these materials provide high strength with a minimum wall thickness. Such thin-walled cannulas provide a greater cross-sectional inflation lumen area than do thicker walled tubes, thereby facilitating flow of inflation fluid through the cannula.

The illustrated distal end assembly 16 includes a balloon 22 which is made of a material suitable for a dilatation balloon, and in accordance with an appropriate molding approach for that material. The balloon 22 is securely attached to an outer body tube 24, which is attached at its other end to the transition assembly 18. Alternately, distal end assemblies can incorporate dual-lumen tubes having parallel rather than coaxial lumens, for example. The illustrated distal end assembly 16 has a coaxial structure. This coaxial structure includes the outer body tube 24 and an inner body tube or guidewire tube 26. A proximal leg portion 28 of the balloon 22 is attached to a distal portion of the outer body tube 24. A distal leg portion 30 of the balloon 22 is secured to a distal portion of the inner body tube 26. The distal end assembly 16 terminates in a distal tip 32. A typical distal end assembly 16 has a length of several centimeters, for example between about 20 cm and about 30 cm.

Distal end assembly 16 also includes a guidewire port 34 at its proximal end. The inner body tube 26 is positioned at this guidewire port 34 so that its proximal opening 36 accommodates a guidewire 38. It will be appreciated that, during use of the illustrated catheter 10 and guidewire 38, the guidewire tube and thus the entire balloon dilatation catheter 10 will be slidably moved with respect to the guidewire 38, after the guidewire 38 has been inserted to the desired location within the vascular system. Operation of the equipment in this regard is generally known.

Referring to the illustrated novel transition assembly 18, it incorporates a floating stiffening member 40. This stiffening member 40 is typically constructed of flat ribbon wire or a wire that is generally round in cross-section. The round cross-section is preferred. A braided or twisted bundle of wires is also possible. Generally, the stiffening member 40 can also be made of materials such as those which are suitable for the proximal cannula 14. Stainless steel is particularly preferred, or possibly nitinol. Stiffening member 40 is preferably designed so that the overall transition assembly 18 retains adequate torsional and column strengths so that twisting, pushing and pulling forces imparted onto the transitional assembly 18 by the proximal cannula 14 will not cause kinking or permanent twisting of the transitional assembly 18. In addition, the flexibility of stiffening member 40 along its length should be selected to provided the desired features and performance, including more smooth flexibility transitions from the proximal cannula 14 to the distal portion 16.

Stiffening member 40 is preferably sealed or affixed at its distal end to the catheter shaft, while the stiffening member 40 proximal end preferably floats within the distal end of the high-strength cannula 14.

A transition tube 42 surrounds most of the stiffening member 40. A proximal end of the transition tube 42 is affixed to the hypotube 14, and distal end of the transition tube 42 is connected to the outer body 24. The transition tube 42 may be typically made of a polymer material. If the tube 42 has good strength attributes, then a less-rigid stiffening 40 member can be provided. Whatever the precise structure utilized, the transition assembly 18 provides a flexible transition between the generally rigid proximal cannula 14 and the generally flexible distal end assembly 16.

With more particular reference to the transition tube 42, it is preferred that the inner diameter of the transition tube 42 define a selected gap distance conforming to the outer diameter of the stiffening member 40, while allowing sliding between the surfaces of the wire 40 and tube 42 so they slidably engage each other during bending along a curve of the inserted guiding catheter. The stiffening member may alternatively have one or more tapered locations, and the transition tube may have its own generally correspondingly shaped and sized tapered locations. Generally, in making the transition assembly 18, the stiffening member 40 is inserted into the inner diameter or lumen of the tubing 42.

In the assembly of the stiffening member 40 and the transition tube 42, the tube 42 is assembled onto the stiffening member 40. In the illustrated embodiment, the proximal end of the transition tube 42 is sealed onto the distal end of the proximal cannula 14. The sealing can be practiced by suitable means, including the use of adhesives and/or heat or other suitable procedures. Similarly, a distal end of the transition tube 42 extends to the distal end of the stiffening member 40, and this distal end is secured to the proximal end portion of the distal assembly 16 at a distal seal area. Conveniently, the proximal guidewire port 34 is formed when the proximal end portion of the guidewire tube 26 and the stiffening wire 40 distal end are sealed between the distal end portion of the transition tube 42 and the proximal end portion of the outer body tube 24.

In the preferred embodiment, the formation of this distal seal area is facilitated by having the outer body tube 24 and the transition tube 42 made of materials which are readily heat-sealed together. The outer body tube 24 can be made, for example, of a nylon material or of a polyamide material, such as an extruded nylon homopolymer or a copolymer or blend of homopolymer and copolymer. In the preferred embodiment, at least a portion of the outer surface of the transition tube 42 is made of a nylon material, and can be made of the same nylon material or polyamide material as the material of which the outer body tube 24 is made. Preferably, at least a portion of the inner surface of the transition tube 42 can be made of a material such as a polyethylene, which more readily bonds to the proximal cannula 14 than does a polyamide or nylon material. In the preferred arrangement, the cannula 14 is made of stainless steel, and the outer body tube 24 is made of nylon 12. In order to accommodate these materials, the transition tube 42 is preferably made of two different materials. The preferred manner of accomplishing this desired result is to have the transition tube 42 be formed as a coextrusion. The coextrusion as an example may provide an inner surface of polyethylene, which bonds well to stainless steel, and an external surface of a nylon material or other material which readily bonds to the distal end assembly.

A typical guidewire tube 26 will preferably accommodate a guidewire 38 having an outer diameter of 0.0014 inch (0.036 mm) when the dilatation catheter 10 is of the percutaneous transluminal catheter angioplasty or PTCA type. When the catheter is, for example, of the percutaneous transluminal angioplasty or PTA type, the guidewire tube 26 will accommodate a guidewire 38 of a larger outer diameter, usually on the order of 0.0018 inch (0.046 mm). When the stiffening member 40 is made of a round stainless steel wire, the diameter of the wire 40 may be selected among various sizes.

FIG. 2 illustrates the stiffening member 40 which extends distally to an extent which helps to protect and strengthen the proximal end portion of the distal end assembly 16, without unduly stiffening the area of joining between the transition assembly 18 and the distal end assembly 16, including the distal seal area. The distal extent of the stiffening wire 40 also assists in avoiding kinking at this joining location where the relatively thick seal area is directly adjacent to thinner tubing lengths.

FIG. 5 provides a somewhat diagrammatic view of the distal area, in that the transition tube 42 and a short filler tube may actually melt together.

Typically, the transition assembly 18 has a total length of between about 10 cm and about 35 cm, preferably between about 12 cm and about 20 cm. The length of the stiffening member 40 can range between about 5 cm and about 30 cm, preferably between about 8 cm and about 18 cm.

It will be appreciated by those skilled in the art that the guiding catheter 20 and the balloon dilatation catheter 10 can comprise a combination of catheters which are used during balloon dilatation procedures such as angioplasty, typically in association with a guidewire 38. With the present invention, the interaction of this combination of catheters is rendered more beneficial to the physician performing a dilatation and/or angioplasty procedure. Without the transition assembly 18 discussed in accordance with the present invention, there may be a tendency for difficulties to arise when attempting to pass the balloon dilatation catheter through the guiding catheter at a location where the guiding catheter has a tight curve at a location along its length within the vascular system and/or heart.

The transition assembly 18 of the present invention is able to navigate a tight bend or curve more easily, and thus imparts a lower lateral force onto the wall of the guiding catheter 20.

It will be understood that the embodiments of the present invention which have been described are illustrative of some of the applications of the principles of the present invention. Various modifications may be made by those skilled in the art without departing from the true spirit and scope of the invention.

What is claimed is:

1. A balloon dilatation catheter comprising:
   a high-strength proximal cannula having proximal and distal ends, and defining a proximal lumen;
   a generally tubular distal end assembly having a guidewire lumen, a balloon member, and an inflation lumen in fluid communication with the proximal lumen of the proximal cannula, the inflation lumen opening into the balloon, the distal end assembly having a flexibility greater than the proximal cannula;
   a transition assembly positioned between and longitudinally connecting the distal end assembly to the proximal cannula, the transition assembly providing flexible bending strain relief, the transition assembly including a stiffening member as well as a transition tube connected to the proximal cannula and the distal end assembly;
   the stiffening member affixed to a distal end of the transition tube near a distal end of the stiffening member, and the stiffening member having a proximal end extending into and floating within the proximal cannula distal end; and
   a guidewire tube affixed to the distal end of the transition tube.

2. The dilatation catheter in accordance with claim 1, wherein the stiffening member of the transition assembly is a flat wire.

3. The dilatation catheter in accordance with claim 1, wherein the stiffening member of the transition assembly is a single wire of circular cross-section.

4. The dilatation catheter in accordance with claim 1, wherein the stiffening member includes a plurality of wires that are twisted or braided together.

5. The dilatation catheter in accordance with claim 1, wherein a distal end portion of the transition tube extends near the distal end of the stiffening member and is secured to the distal end assembly.

6. The dilatation catheter in accordance with claim 1, wherein the transition tube of the transition assembly extends proximally to and is secured to the distal end of the proximal cannula.

7. The dilatation catheter in accordance with claim 6, wherein a distal end portion of the transition tube is secured to the distal end assembly, wherein the transition tube has an internal surface and an external surface, and wherein the distal end of the proximal cannula is secured to the inside surface of the transition tube, while the proximal end of the distal end assembly is secured to the outside surface of the transition tube.

8. The dilatation catheter in accordance with claim 7, wherein the transition tube is a coextruded tube having an inner surface of a material which is readily bondable to the proximal cannula, and having an outer surface of a material which is readily bondable to the distal end assembly.

9. The dilation catheter in accordance with claim 1, further including a proximal guidewire port generally at a location where the transition assembly is secured to the distal end assembly.

10. The dilation catheter in accordance with claim 1, in which the stiffening member extends distally beyond a proximal end of the distal end assembly.

11. The balloon dilatation catheter of claim 1, wherein the high-strength proximal cannula is a metal hypotube.

12. A balloon dilatation catheter and guiding catheter system, comprising:
    a guiding catheter having a length suitable for dilatation procedures, the guiding catheter having a distal tip portion and a guiding lumen with an inner diameter, said distal tip portion having a distal opening;
    a balloon dilatation catheter having a series of components, each with an outer diameter smaller than the inner diameter of the guiding catheter to permit longitudinal sliding of the balloon dilatation catheter within the guiding catheter and out of the opening of the guiding catheter distal opening, including:
    a high-strength proximal cannula having proximal and distal ends, and defining a proximal lumen;
    a generally tubular distal end assembly having a guidewire lumen, a balloon member, and an inflation lumen in fluid communication with the proximal lumen of the proximal cannula, the inflation lumen opening into the balloon, the distal end assembly having a flexibility greater than the proximal cannula;
    a transition assembly positioned between and longitudinally connecting the distal end assembly to the proximal cannula, and providing flexible bending strain relief, the transition assembly including a stiffening member and a transition tube surrounding a portion of the stiffening member; and
    the stiffening member affixed to a distal end of the transition tube near a distal end of the stiffening member, and having a proximal end extending into and floating within the proximal cannula; and
    a guidewire tube affixed to the distal end of the transition tube.

13. The catheter system in accordance with claim 12, wherein the stiffening member of the transition assembly is a single wire.

14. The catheter system in accordance with claim 12, wherein the transition tube of the transition assembly is secured to the distal end of the proximal cannula.

15. The catheter system in accordance with claim 14, wherein a distal end portion of the transition tube secured to the distal end assembly, the transition tube having an internal surface and an external surface, and wherein the distal end of the proximal cannula is secured to the inside surface of the transition tube, while the proximal end of the distal end assembly is secured to the outside surface of the transition tube.

16. The catheter system in accordance with claim 15, wherein the transition tube is a co-extruded tube having an inner surface of a material which is readily bondable to the proximal cannula.

17. The catheter system in accordance with claim 12, further including a proximal guidewire port generally at a location where the transition assembly is secured to the distal end assembly.

18. The balloon dilatation catheter and guiding catheter system of claim 12, wherein the high-strength proximal cannula is a metal hypotube.

* * * * *